United States Patent [19]

Merchant

[11] Patent Number: 5,564,438
[45] Date of Patent: Oct. 15, 1996

[54] METHOD AND APPARATUS FOR PRONE POSITION RADIATION THERAPY OF THE BREAST

[76] Inventor: Thomas E. Merchant, 402 E. 64th St., New York, N.Y. 10021

[21] Appl. No.: 103,506

[22] Filed: Aug. 9, 1993

[51] Int. Cl.$^6$ ............... A61G 15/00; A61B 6/04
[52] U.S. Cl. ............................. 128/845; 378/37
[58] Field of Search ............ 378/37, 65; 128/845, 128/846, 763; 604/74, 75, 73; 250/451

[56] References Cited

U.S. PATENT DOCUMENTS

| | | | |
|---|---|---|---|
| 3,165,630 | 1/1965 | Bielat et al. | 250/58 |
| 3,556,081 | 1/1971 | Jones | 378/37 |
| 3,578,971 | 5/1971 | Lasky | 378/37 |
| 3,963,933 | 6/1976 | Henkes, Jr. | 250/456 |
| 3,973,126 | 8/1976 | Redington | 378/37 |
| 4,051,380 | 9/1977 | Lasky | 250/451 |
| 5,078,142 | 1/1992 | Siczek et al. | 128/653.1 |

FOREIGN PATENT DOCUMENTS 2068700  8/1981  United Kingdom.

*Primary Examiner*—Michael A. Brown
*Attorney, Agent, or Firm*—James C. Scott

[57] ABSTRACT

A method and apparatus for prone position radiation therapy of breast tissue wherein a patient is placed in a prone position upon a platform positioned upon a radiation accelerator table of a radiation therapy accelerator machine to effectively isolate the breast tissue to be irradiated from the rest of the body. A top surface of the platform includes an aperture and/or adjustable opening through which the breast to be irradiated is inserted to hang freely and pendulously through the platform in an open space treatment field over the top of the accelerator table. The breast so positioned is free of contact with the platform and table and can be irradiated from all accessible angles of the accelerator head of the accelerator machine relative to the accelerator table without interference or obstruction by the platform and without any radiation incident upon untargeted portions of the patient's body.

15 Claims, 5 Drawing Sheets

METHOD AND APPARATUS FOR PRONE POSITION RADIATION THERAPY OF THE BREAST

FIELD OF THE INVENTION

The invention relates generally to radiation therapy and, more particularly, to radiation therapy of breast tissue.

BACKGROUND OF THE INVENTION

Radiation therapy is widely performed on patients with breast tissue affected, for example, with cancerous cells and following breast conserving surgery. The acute toxicity, long-term side effects, and cosmetic outcome of such treatment are attributable to a number of factors including technical aspects of surgery, pre-existing systemic medical conditions, the use of specific chemotherapeutic agents and administration of such relative to delivery of radiation therapy, radiation therapy treatment technique, and patient morphology. Patient morphology is generally the most difficult factor to compensate for in seeking optimum delivery of radiation therapy and a factor which most directly affects cosmetic outcome.

Optimal radiotherapy technique is described as 4500–5000 cGy to the whole breast over a period of 4.5–5 weeks, followed by a boost to the excisional biopsy site with an additional 1000–1500 cGy. The technical aspects of delivering radiation therapy as a part of breast conserving therapy are less well defined and have evolved as a function of technical innovation and studies examining the patterns of failure. Improvements in methods for field matching, the abandonment of routine regional nodal irradiation, controversies concerning the necessity and method for boost treatment, sequencing of chemotherapy, and indications for radiation therapy, have distracted the radiation oncologist from attempting technical improvements in the delivery of radiation therapy.

Treatment simulation and set-up are carried out primarily with the patient in the supine position, although certain cancer centers continue to use the decubitus position as their standard treatment position. When patients with large breasts are encountered, the decubitus position is sometimes used as an alternative to the supine position. While the supine position is considered more reproducible, it irradiates more lung and requires the use of wedge filters, high energy radiation beams, and bolus to overcome non-homogeneous dose distributions and skin overdose. The decubitus technique is performed with the breast tissue compressed to an even thickness of 6–8 cm and results in a more homogeneous dose distribution. The decubitus technique requires meticulous positioning and protection of the contralateral breast; it is therefore considered less reproducible and lacks the flexibility of supine position treatment, especially when nodal irradiation is considered. For these reasons, the decubitus technique is seldom used and has dropped from favor.

Women with large and/or pendulous breasts, or women with small to medium size breasts and unusual chest wall contours, have relatively large medial to lateral separations. The separation is defined as the measure transverse distance across the base of the breast which will require radiation therapy. Such patients require modifications and alterations to traditional treatment techniques. When treatment is carried out in the supine position, the transverse displacement of breast tissue over the anterior chest wall creates a large separation. This separation, combined with potential folding of the breast at its most caudal extent, are two of the aspects of breast radiation therapy that contribute to non-uniformity of dose distributions and irradiation of large volumes of lung and heart tissue. A number of technical modifications have been proposed to improve the dose distribution in women with large separations. These modifications include the use of wedge filters, high-energy photon beams, beam-spoilers and bolus but which do not entirely or satisfactorily overcome the above described disadvantages and dangers.

As mentioned, an alternative method of administering such therapy is to have the patient fully reclined in the decubitus position upon a horizontal surface and to position the radiation energy source adjacent the surface of tissue to be treated. Because this method does not physically isolate the part to be treated by radiation, it has the serious disadvantage of irradiation of tissue other than the affected portion of the breast and further including heart, lung and skin tissue proximate to the breast, all resulting from the patient being in the decubitus position. These and other associated problems are especially acute in patients with large breasts and/or pulmonary or cardiac conditions to whom scattered and excessive radiation creates significant risks.

SUMMARY OF THE INVENTION

The present invention overcomes these and other disadvantages of methods and apparatus heretofore used in radiation therapy of breast tissue. The method of the present invention orients the patient in an optimum position for breast irradiation with opposed, tangential or non-coplanar beams which encompass the entire breast and minimize the volume of normal tissue within the radiation therapy portal.

The method of the present invention includes the use of external beam radiation therapy for treatment of breast cancer with the patient in a prone position so that the breast to be irradiated hangs pendulously in a dependent manner away from the chest wall. With the patient so positioned, the radiation therapy beams are directed to the breast to be treated. This method improves dose distribution within the irradiated breast and reduces skin toxicity and dose to normal tissues such as the lung and heart. The method includes the steps of positioning a patient in a prone position upon a breast radiation therapy platform positioned on top of an accelerator table, positioning the breast to be treated through an aperture in the top surface of the platform, to hang pendulously and freely in an open space above the top of the accelerator table, not in contact with the platform or table, and directing radiation beams to the breast so positioned. The method may further include the step adjusting the position of the patient upon the platform by the use of cushions or other supportive devices to optimally position the breast to be irradiated. The method may further include the step of radiographing or tattooing the breast once positioned through the aperture of the platform to further improve the accuracy and dose distribution of the radiation.

The apparatus of the present invention is a breast radiation therapy patient supporting and positioning platform which has a generally horizontal patient body supporting portion adapted to fit upon and be elevated above the surface of a radiation accelerator table, and an opening in the top surface of the platform positioned and shaped for insertion of one of a patient's breasts therethrough so that the breast hangs in a pendulous dependent manner, not in contact with the platform or accelerator table, below the top surface of the platform.

To the accomplishment of the foregoing and related ends the invention then comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

The following detailed description of the invention is made with reference to the accompanying drawings wherein like reference numerals refer to like parts and.

DESCRIPTION OF PREFERRED METHODS AND EMBODIMENTS

Figure 1:
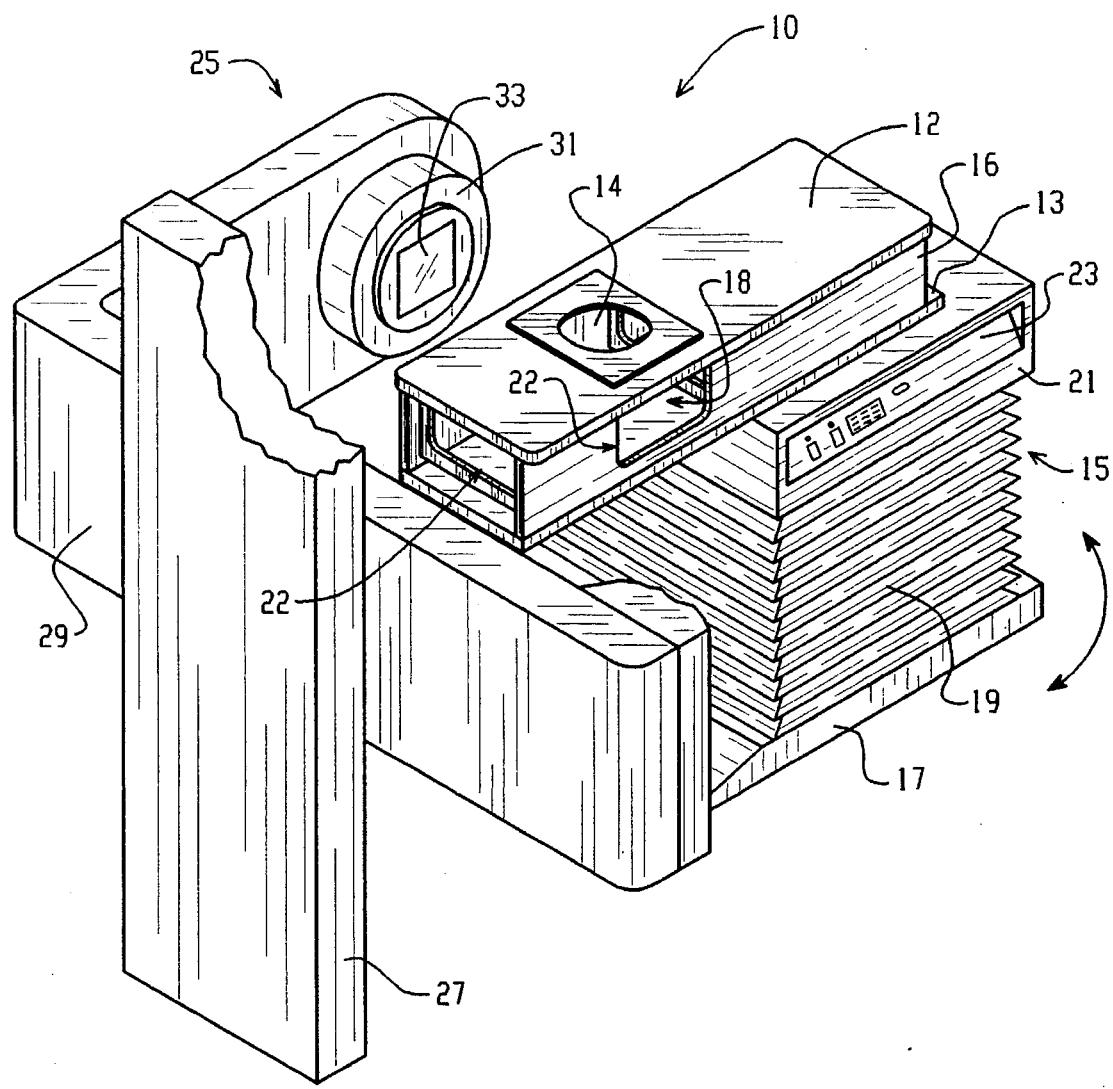
FIG. 1 is a perspective view of an embodiment of a radiation therapy platform in accordance with the present invention installed upon a radiation accelerator table adjacent an accelerator machine.

In the method of this invention the patient lies prone on a treatment platform, indicated in FIG. 1 generally at 10, which has a substantially horizontal supporting surface 12 and is adapted to fit upon a patient supporting surface 13 of an accelerator table, indicated generally at 15. The supporting surface 12 of the platform 10 can be, for example, generally in the form of rectangle having a length and width approximately equal to the top of the patient supporting surface 13 of accelerator table 15 to adequately support and position patients of all sizes in a prone position as described.

The accelerator table 15 includes a 360 degree horizontal swivel adjustable base 17, a vertically adjustable table supporting frame 19, a horizontally adjustable table top 21 with a control panel 23 incorporated therein, and the patient supporting surface 13 operatively connected to the horizontal plane adjustment mechanism of table top 21. The patient supporting surface 12 of platform 10 is elevated above the surface 13 of accelerator table 15 a determined distance by vertical support walls 16 as described below.

The platform 10 is shown positioned upon accelerator table 15 which is in an operative arrangement with an accelerator machine, indicated generally at 25. The accelerator machine 25 used in connection with this invention may be of the vertically mounted 360 degree rotatable type as shown such as, for example, a CLINAC 600C manufactured by Varian Corporation. Accelerator machines of this type consist basically of a vertical floor mounted stand 27 and an accelerator head supporting arm 29 pivotably axially mounted upon stand 27 and having a right angle bend to allow 360 degree positioning in a vertical plane of the beam emitting face 33 of accelerator head 31, mounted at an end of supporting arm 29, about the patient supporting surface 13 of accelerator table 15. With the platform 10 in position upon the patient supporting surface 13 of accelerator table 15 as described, the 360 degree rotatable accelerator head 31 can be positioned at all points radially in a vertical plane about the portion of the patient and platform 10 positioned to extend beyond the end of accelerator table base 17 toward the accelerator head supporting arm 29. By horizontal rotation of accelerator table base 17 as indicated, the position of the patient and platform can be adjusted in a horizontal plane relative to accelerator head 33. Thus it is disclosed that all of the vertical and horizontal adjustments of the accelerator machine 17 relative to accelerator table 15 can be made with the platform 10 in position upon the accelerator table 15 as shown. Moreover, a breast suspended from a prone position into platform 10 can be irradiated, without any obstruction or interference from the patient supporting surface 13 of accelerator table 15, from all positions of adjustment of the accelerator head 33 relative to accelerator table 15. It will further be appreciated that the method and apparatus of this invention can be used with any suitable source of radiation which can be suitably positioned to direct radiation beams to the treatment field of the platform in portals of suitable geometry as described.

The supporting surface 12 of platform 10 includes an aperture 14 through which a single breast is positioned to hang in a dependent manner below supporting surface 12 into a treatment field 18. The aperture 14 may consist simply of a hole in surface 12, a hole in a removable template, or an adjustable slot as described below which allows the entire breast to hang therethrough and a portion of the chest wall behind the breast to sag away from the thorax. It is noted that a breast so positioned through the aperture 14 is freely suspended and not in contact with either the platform 10 or the accelerator table 15. This configuration optimizes the shape and positioning of the breast for isolated radiotherapy without interference from the surrounding apparatus or the chest wall.

Figure 2:
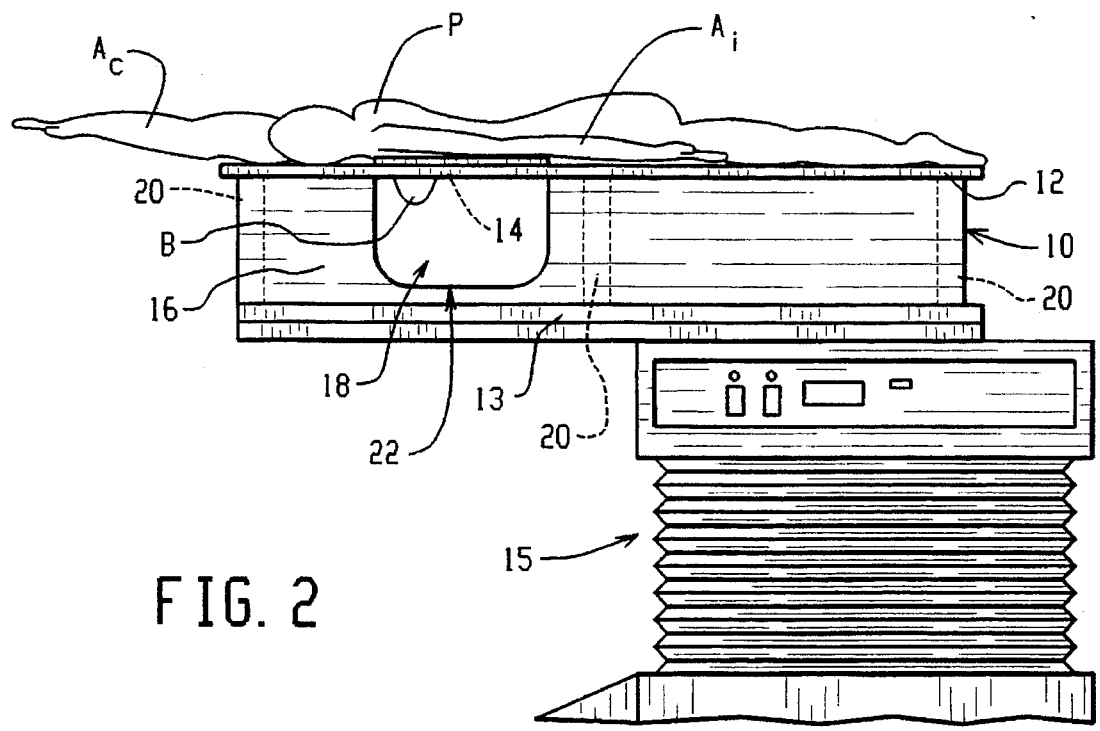
FIG. 2 is a side view of an embodiment of a radiation therapy platform in accordance with the present invention installed upon a radiation accelerator table.

In FIG. 2, a patient P is shown in the prone position upon supporting surface 12 of platform 10 with one breast B positioned through aperture 14. In this position, substantially all of the tissue of the breast B and a portion of the anterior chest wall positioned through aperture 14 is isolated within a treatment field 18 defined as the open space below supporting surface 12 and above the patient supporting surface 13 of accelerator table 15. The breast B is isolated from the remainder of the patient's body and is not in contact with the platform 10 or table 15. Importantly, this position allows the clinically determined medial and lateral aspects of the breast tissue to be included within the projection of radiation portals emitted from accelerator head 31 at treatment field 18 through windows 22 in the vertical support walls 16.

It will be appreciated by those skilled in the art and familiar with breast radiation therapy equipment, and in particular the equipment of Varian Corporation described as used in connection with this invention, that the prone position breast radiation therapy method of this invention could not be performed on accelerator machines of this type without the use of platform 10 for the reason that vertical height adjustment of the accelerator table 15 is limited to an extent too low to allow direction of beam portals underneath the patient supporting surface 13. Furthermore, the presence of metallic frames at the edges of the patient supporting surface 13 prevents and otherwise interferes with laterally directed radiation portals to a breast suspended from the prone position.

The method may further include the treatment planning and preparation steps of optimally positioning the patient's arms with, for example as shown in FIG. 2, the ipsilateral arm $A_i$ placed along the side of the patient's body and the contralateral arm $A_c$ raised above the head. Similar approaches to positioning the patient upon the treatment platform can be used and in any combination that results in a reproducible set-up and as consistent treatment as possible. Such optimum positioning can be predetermined in a simulation set-up on a simulator couch or examination table.

Simulation and treatment planning in practicing the method of the invention involve many of the steps as normally required for the simulation of treatment of a patient for breast-only radiation, as is well known in the art. For example, such steps include immobilization, selection of an optimal size and shape of aperture 14 in supporting surface 12 to allow for the breast and a portion of the chest wall to be inserted therethrough and hang below supporting surface 12, simulation of specific beam arrangements, and tattoos placed at the field edges on the chest wall laterally and medially. A transverse contour is taken at the level of the medial and lateral field centers with the patient in the treatment position to determine the dose distribution by conventional means. The platform 10 can also be mounted on, for example, a simulator couch or examination table for testing and measurement purposes in preparation for radiation therapy treatment.

Figure 3:
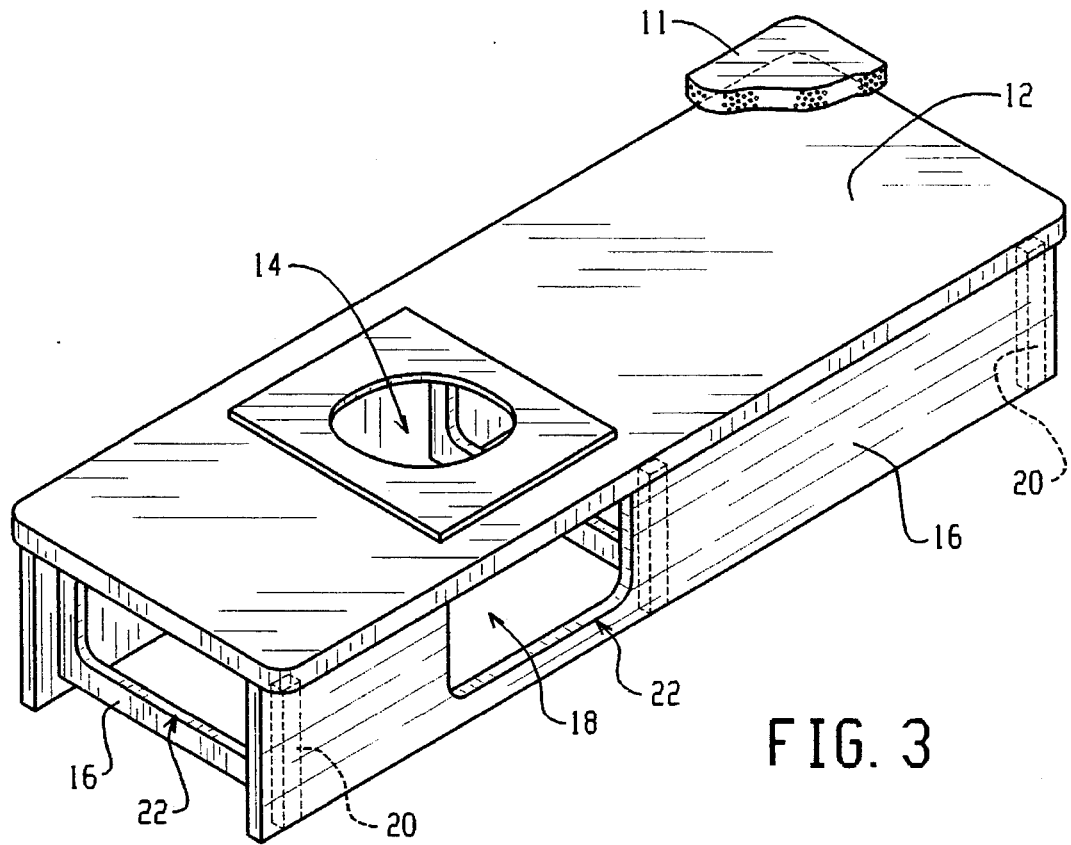
FIG. 3 is a perspective view of an embodiment of a radiation therapy platform in accordance with the present invention.

As shown in FIG. 2 and FIG. 3, the supporting surface 12 of the treatment platform 10 is held in position above the accelerator table 15 by vertical side and end support walls 16. The vertical support walls 16 can be, for example, attached perpendicularly along the periphery of the supporting surface 12 of the treatment platform 10 and at the bottom edge adapted to fit upon or be permanently attached to patient supporting surface 13. Alternatively, the platform 10 can be adapted to fit upon the patient supporting surface of an accelerator table in a cantilevered manner wherein the platform extends over an end of the accelerator table. The vertical support walls 16 further include at least one or more windows 22 in the side and/or end walls through which lateral, tangential, and/or opposed radiation beams are directed to the breast positioned through aperture 14. The size of the windows 22 is selectively chosen to correspond to and in part define the desired size of the treatment field 18 and the direction/deflection of the radiation beams passing therethrough. Structural support members 20 (shown in phantom) may also be provided, for example, at the corners and along the length of supporting surface 12 within vertical support walls 16 and be adapted to mount upon a frame of the patient supporting surface 13 of accelerator table 15. The supporting surface 12 and vertical support walls 16 can be made of any radiation compatible material having suitable weight-bearing strength. The support walls 16 can be made of or include portions made of transparent material to enable visual verification of the patient position within treatment field 18 and the position of a radiation source relative to windows 22.

An optimum height of the supporting surface 12 of the platform 10 above patient supporting surface 13 has been determined according to a mean average distance a large or pendulous breast will hang through aperture 14. I have determined that a vertical clearance of the supporting surface 12 over the patient supporting frame 13 of approximately 30 centimeters is sufficient for most patients. This dimension is determined with regard to the fact that the patient supporting surface 13 of the top of the accelerator table 15 on most accelerator tables cannot be elevated (by vertical adjustment) sufficiently to allow for pendulous suspension of the entire breast in the manner disclosed to give lateral beam access to a breast suspended from a prone position below the surface of the table. Therefore, without extensive and unobvious modifications, accelerator tables of this type would not allow patients to be treated in the prone position without the use of the platform and method of this invention. A booster section (not shown) having the same length dimensions of support walls 16 and a height of, for example, 10 cm may be inserted between the bottom ends of the vertical support walls 16 and the patient supporting frame 13 to increase the height of the patient supporting platform 12 over the accelerator table 15 to accommodate extra large patients.

As shown in FIG. 3, the supporting surface 12 of the platform 10 may simply have a flat surface and a circular or ovoid opening as aperture 14, positioned for example along the longitudinal centerline of supporting surface 12, for a breast and portion of anterior chest wall to sag therethrough into treatment field 18. The supporting surface 12 may be removable from vertical support walls 16 to facilitate repositioning of the aperture 14 or to allow interchange with a different supporting surface having a different configuration and/or different aperture as described below. The supporting surface 12 may also include padding 11 which may be contoured, particularly in the area of aperture 14 for comfort and to properly position the patient to optimize the morphology of the breast positioned through the aperture.

Figure 4:
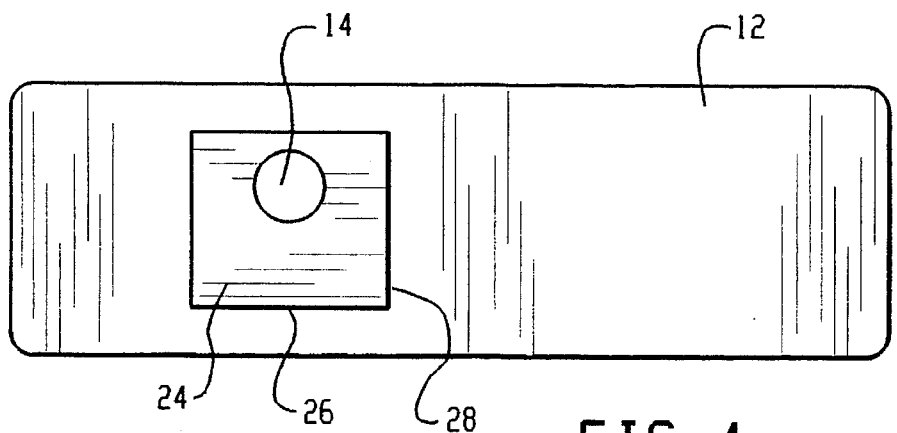
FIG. 4 is a top view of another embodiment of a radiation therapy platform in accordance with the present invention.

As shown from above in FIG. 4, in one version of the supporting surface 12 of the platform 10, the aperture 14 is formed within a removable template 24 which fits substantially flush within the supporting surface 12 in template receiving cutout 26. In this manner, multiple templates 24 having the same outer dimensions to fit receiving cutout 26 but with different sized and shaped apertures 14 can be used in connection with a single platform 10 to accommodate a wide range of chest and breast anatomies. The templates 24 may be constructed of a suitable transparent material to allow for visual verification of the position of the breast and anterior chest wall through the aperture 14. The periphery 28 of the aperture 14 may have a padding of a soft, malleable material such as foam padding or plastic for patient comfort and to assist in achieving the desired tissue contour at the base of the breast.

Figure 5:
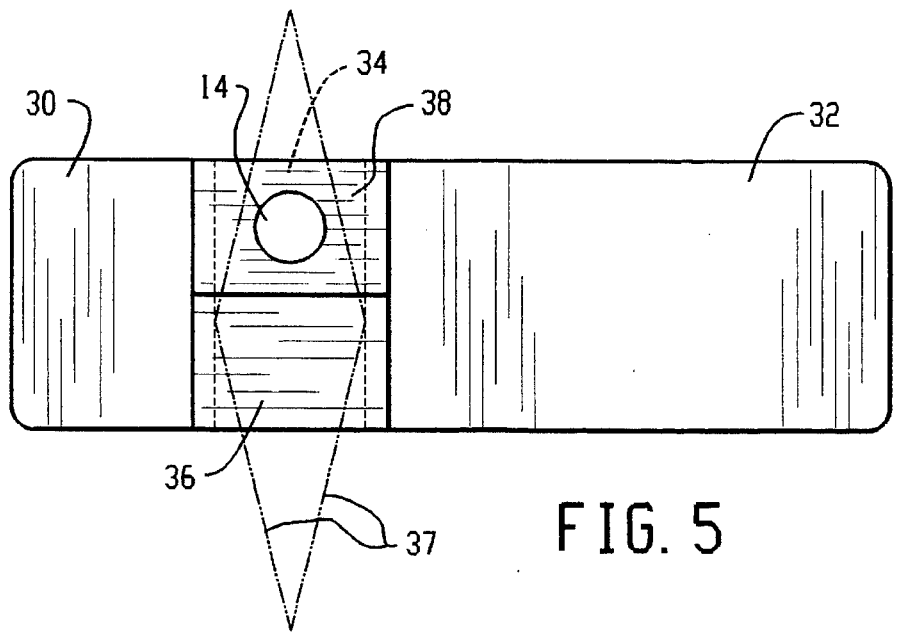
FIG. 5 is a top view of another embodiment of a radiation therapy platform in accordance with the present invention.
Figure 6:
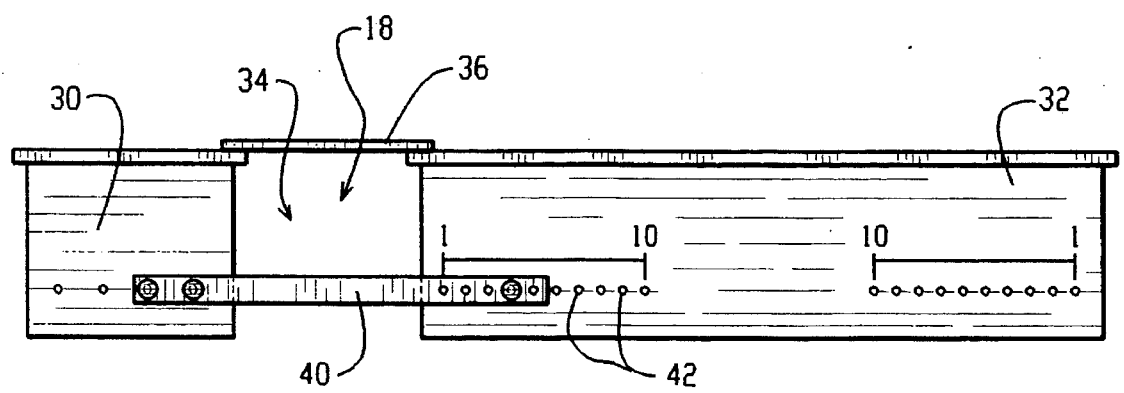
FIG. 6 is a side view of the embodiment of the platform of FIG. 5.

FIG. 5 and FIG. 6 illustrate another embodiment of a platform 10 which has at least one longitudinally adjustable end section 30 which, when extended away from a main section 32, forms a slot 34 into which a patient's breast is suspended into the treatment field 18. The breast not to be examined retained at the supporting surface 12 by a padded board 36 approximately positioned with an inward lateral edge thereof at the medial chest. Lateral opposed radiation beams, directed for example along beam path lines 37, are directed into the lateral openings of slot 34 into treatment field 18. A second board 38, similar to template 24 and containing aperture 14, can optionally be provided at the supporting surface 12 adjacent padded board 36 and about the suspended breast to be irradiated. The edges of main section 32 and end section 30 adjacent the top opening of slot 34 can be rounded and/or padded or otherwise adapted to include flexible material to improve patient comfort and achieve the desired contour at the base of the breast and chest wall.

As shown in FIG. 6, end section 30 can be mechanically connected to main section 32 by adjustment guides 40 attached horizontally along the exterior of the vertical support walls 16, out of the radiation beam path, at linearly calibrated fixing points of adjustment 42 which can be labelled to indicate the corresponding slot width. The slot width is thereby selected and fixed in position to best accommodate each patient and the adjustment point recorded on the patient's record to facilitate ready reproduction of the treatment set-up.

Figure 7:
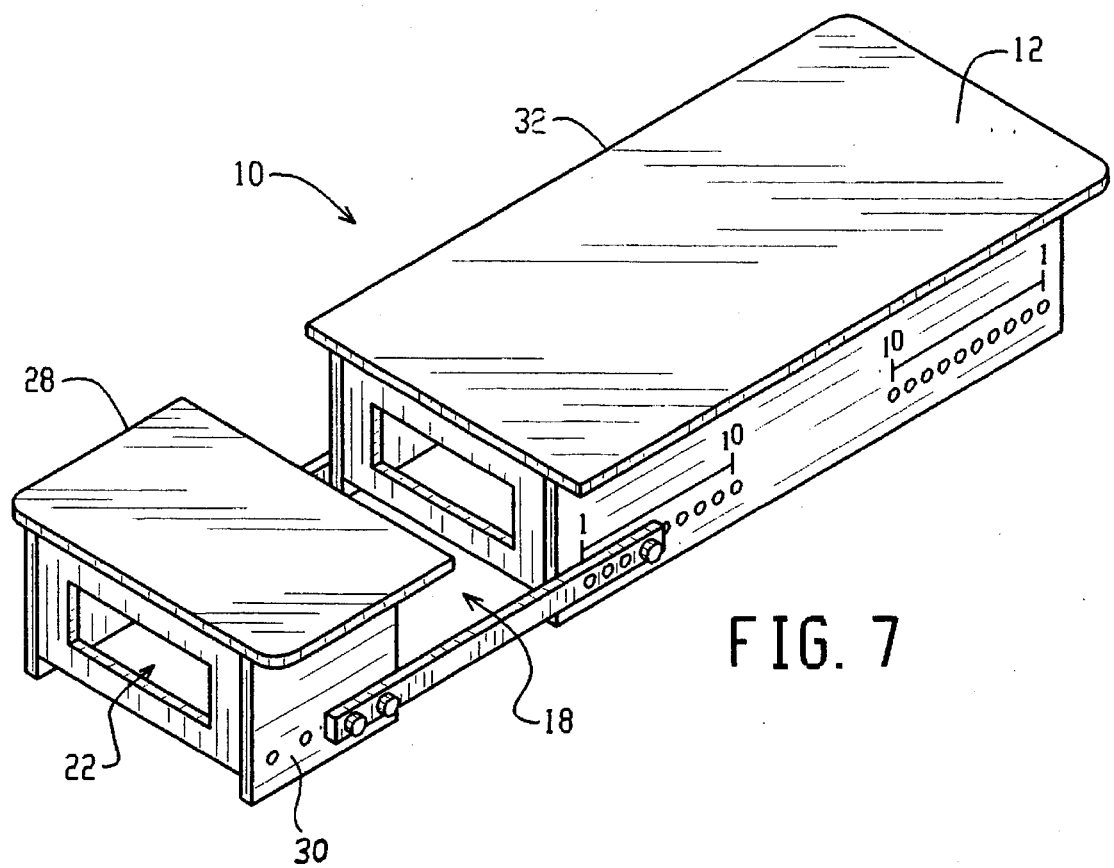
FIG. 7 is a perspective view of the embodiment of the platform of FIGS. 5 and 6.
Figure 11:
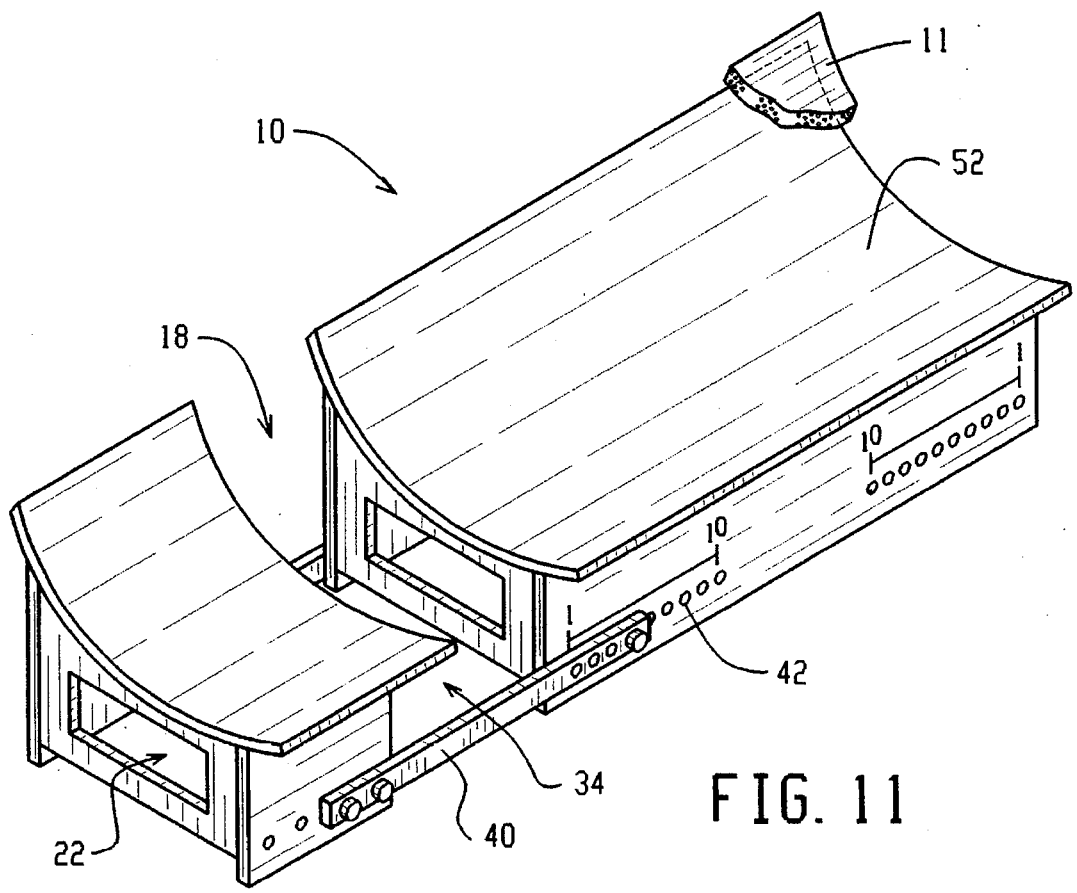
FIG. 11 is a perspective view of another embodiment of a platform in accordance with the present invention.

As shown in FIGS. 3, 7 and 11, each of the embodiments of the platform 10 may also include windows 22 in the end vertical support walls 16 so that radiation beams may be directed longitudinally through the interior of the platform into treatment field 18.

Figure 8:
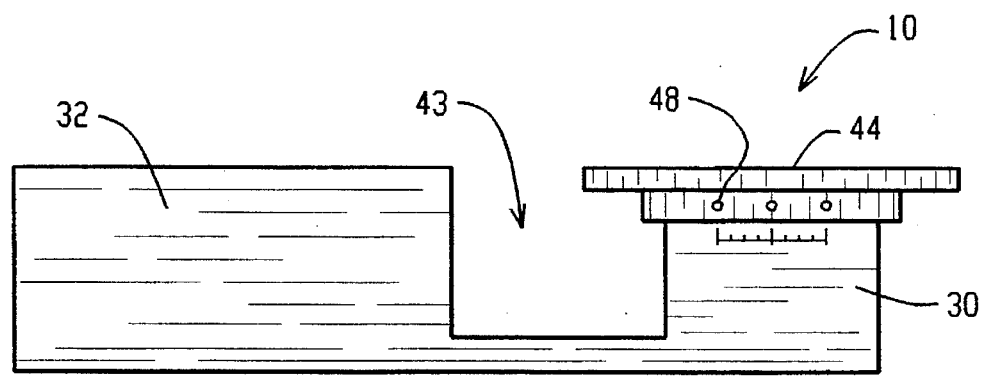
FIG. 8 is a side view of another embodiment of a radiation therapy platform in accordance with the present invention.
Figure 9:
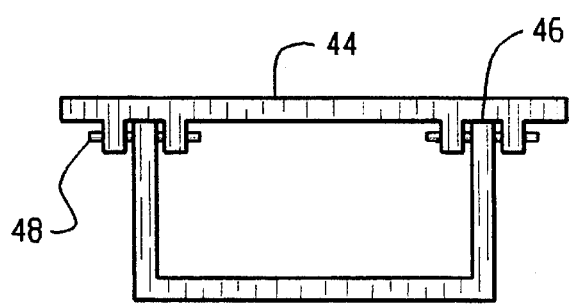
FIG. 9 is an end view of the embodiment of the platform of FIG. 8.

FIG. 8 illustrates another embodiment of a platform 10 having a longitudinally adjustable patient supporting surface 44 which slides horizontally over the top of end section 30 to thereby adjust the size of opening 43 relative to main section 32. Longitudinally adjustable patient supporting surface 44 can, for example, slide along the top edges 46 of vertical support walls 16 as shown in FIG. 9 and be locked into the desired position by throughhole locking pin mechanism 48. Throughholes for locking pin mechanism 48 can be calibrated and labelled similar to adjustment points 42 to reproduce treatment set-ups with this embodiment of the platform. Alternatively and more preferably, an infinite adjustment system can be provided for the supporting surface 44 relative to end section 28 whereby set screws are provided in place of locking pin 48 to be screw tightened against the outer surface of vertical support walls 16.

Figure 10:
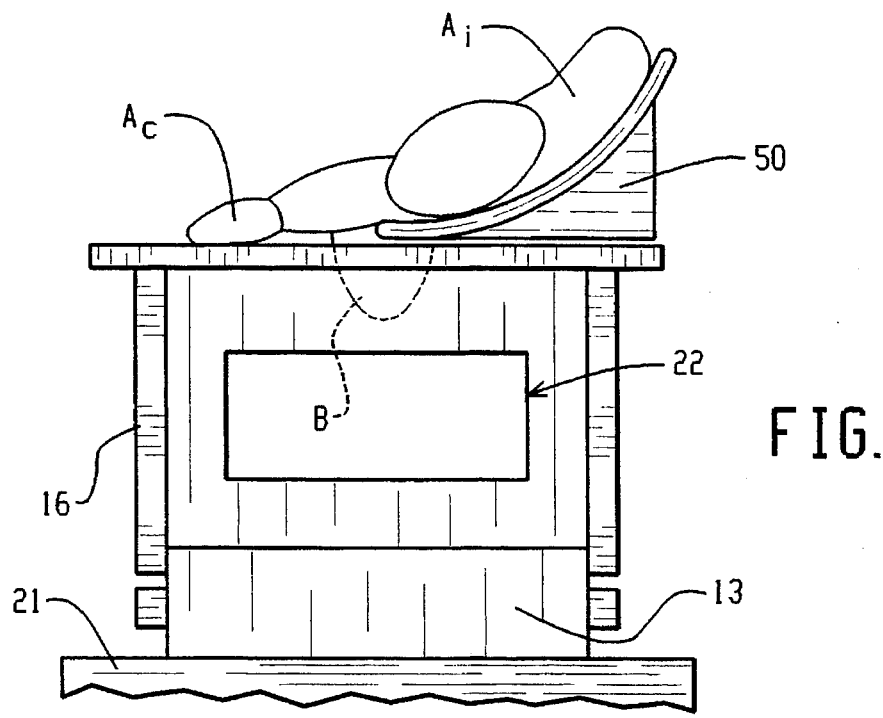
FIG. 10 is an end view of a platform in accordance with the present invention in combination with a patient supporting cushion.

In each of the embodiments thus far described, a laterally upward curved patient positioning cushion 50 can be used under the ipsilateral arm $A_i$, as shown in an end view of the platform 10 in FIG. 10, to move the arm and shoulder up and away from the supporting surface 12 of the platform 10. This allows for improved visual verification of patient and breast position with respect to the platform and the radiation source and can also improve the morphology of the breast positioned through aperture 14. The cushion 50 can be made of flexible malleable material such as for example plastic and/or netting to improve adjustment of the position of the breast and chest wall.

FIG. 11 illustrates another embodiment of the platform 10 which structurally incorporates the advantage of the laterally upward curved cushion 50 into the supporting surface of the platform. In this embodiment, a laterally upward curved supporting surface 52, having a curvature similar to cushion 50, is provided along the entire length of the supporting surface 12 of the platform so that the patient's entire body is positioned at the lateral angle as shown in FIG. 10 which allows for the treated breast to be more easily and comfortably positioned suspended in the middle of slot 34, palpated, radiographed and tattooed. The laterally upward curved supporting surface 52 can also be incorporated into the embodiment of FIGS. 3 and 4 and 8 wherein aperture 14 of appropriate shape is provided in the curved supporting surface 52.

In order to obtain a minimum radiographic isocenter of the target breast at 100 centimeters for isocentric technique, the block tray accessory of the accelerator head 31 (on the Clinac 600C) must be removed for the treatment to be carried out. Verification of treatment requires that portal films be taken and compared with plain films taken at the time of simulation. The ribs are the most reliable radiographic landmark and provide the radiation oncologist with a general idea of the amount of chest wall, lung and heart that fall within the treatment portals (i.e., below the supporting surface 12).

In order to verify the position of the chest wall with respect to the edge of the treatment field, and to determine the amount lung and myocardium irradiated with the prone position treatment, MR images or CT scans of the patient can be obtained in both prone and supine positions prior to initiating treatment by the method of this invention. This allows comparison of dose volume histograms for the two treatment positions and to obtain contours at positions other than at the axial center of the treatment fields.

Although the invention has been shown and described with respect to certain preferred embodiments, it is obvious that equivalent alterations and modifications will occur to other skilled in the art upon reading and comprehension of this specification. The present invention includes all such equivalent alterations and modifications, and is limited only by the scope of the following claims.

I claim:

1. A breast radiation therapy platform in combination with a position adjustable radiation therapy accelerator table for positioning a patient to receive therapeutic radiation to breast tissue, the combination comprising, a radiation therapy accelerator table having a generally flat position adjustable patient supporting surface, a breast radiation therapy platform having a body supporting portion adapted to fit upon and be elevated over the patient supporting surface of the position adjustable radiation therapy accelerator table, said body supporting portion of said breast radiation therapy platform having an opening for suspension of a breast to hang freely through the opening and below said body supporting portion in an open space over said surface of said radiation therapy accelerator table.

2. The combination of claim 1 wherein the breast radiation therapy platform positioned upon the radiation therapy accelerator table is movable in unison with the table to all possible adjustable positions of the table, with a distance of the body supporting portion elevated over said radiation therapy accelerator table remaining fixed.

3. The breast radiation therapy platform of the combination of claim 1 wherein a breast positioned through said opening of the platform positioned upon the radiation therapy accelerator table is freely suspended in an open space above a top surface of a said table and not in contact with the platform or table.

4. The breast radiation therapy platform of the combination of claim 1 wherein said opening is a single substantially circular hole in the body supporting portion.

5. The breast radiation therapy platform of the combination of claim 1 wherein said opening is comprised of a cut-out portion and a removable template having the opening formed in said template.

6. The breast radiation therapy platform of the combination of claim 5, wherein different templates having different sized openings can be inserted into said cut-out portion.

7. The radiation therapy platform of the combination of claim 1 wherein said body supporting portion is supported over said accelerator table by vertical support walls having openings through which therapeutic radiation can be directed into said platform to a breast positioned through said opening.

8. The breast radiation therapy platform of the combination of claim 1 wherein said opening is adjustable in size.

9. The breast radiation therapy platform of the combination of 8 wherein said opening is adjustable in size by sliding adjustment of a portion of said body supporting surface along a top edge of said vertical support walls.

10. A platform for positioning a patient to receive breast radiation therapy comprising, a patient supporting surface attached to an elevating support structure adapted to fit upon a radiation accelerator table to elevate said patient supporting surface over a top surface of said table, said patient supporting surface having a generally circular breast opening for suspending a breast untouched in open space through said opening and not in contact with said platform with the patient in a prone position, said support structure having openings therein to allow radiation beams to be directed laterally through said structure to be incident upon a breast positioned through said opening.

11. The platform of claim 10 wherein said patient supporting surface is partially laterally upwardly curved on one side relative to the length of the platform with the opening approximately positioned at a low end of the curve where the curve merges with a substantially flat portion of the patient supporting surface.

12. The platform of claim 10 wherein the patient supporting surface is padded with a pad contoured to optimally form the breast position through said breast opening.

13. A method of administering therapeutic radiation to the breast comprising the steps on:

positioning a patient prone upon a substantially horizontal patient supporting surface elevated and supported over a radiation accelerator table, positioning one of the patient's breasts through an opening the patient supporting surface so that the breast hangs freely below said surface and is not in contact with said platform or said table and is isolated from the patient's body in an area of free space over the top of said radiation accelerator table to receive therapeutic radiation from a radiation source, positioning a malleable material around the base of the breast positioned through the opening to optimally shape the breast receiving radiation therapy, and positioning a radiation source relative to the breast positioned through the supporting surface and delivering therapeutic radiation to the breast.

14. The method of claim 13 further including the step of positioning an arm of the patient contralateral to the breast to receive radiation above the patient's head.

15. The method of claim 13 further including the step of positioning a laterally upwardly curved cushion between patient's body and the patient supporting platform along a the patient opposite the side of the breast positioned through the opening.

* * * * *